United States Patent
Hanada et al.

(10) Patent No.: US 7,438,793 B2
(45) Date of Patent: Oct. 21, 2008

(54) CAPILLARY ARRAY HAVING LOAD HEADER

(75) Inventors: Toshio Hanada, Hitachinaka (JP); Ryoji Inaba, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 601 days.

(21) Appl. No.: 10/812,004

(22) Filed: Mar. 30, 2004

(65) Prior Publication Data

US 2004/0251138 A1  Dec. 16, 2004

(30) Foreign Application Priority Data

Mar. 31, 2003  (JP) .............................. 2003-095302

(51) Int. Cl.
*G01N 27/453*  (2006.01)

(52) U.S. Cl. ...................................... 204/604; 204/601

(58) Field of Classification Search ......... 204/601–605, 204/451–455
See application file for complete search history.

(56) References Cited

U.S. PATENT DOCUMENTS 5,885,430 A * 3/1999 Kernan et al. ................ 204/453
6,878,256 B2 * 4/2005 Kasai et al. .................. 204/604

FOREIGN PATENT DOCUMENTS

| JP | 62-143260 | 9/1987 |
| JP | 2002-71642 | 3/2002 |
| JP | 2002-365262 | 12/2002 |

* cited by examiner

*Primary Examiner*—Alex Noguerola
(74) *Attorney, Agent, or Firm*—Dickstein Shapiro LLP

(57) ABSTRACT

A multi-capillary array which can be used for a multi-capillary electrophoresis apparatus to effectively disperse the heat generated within a load header. In a load header of the capillary array used for the multi-capillary electrophoresis, an insulated holder, a connection plate and tubular electrodes are closely arranged without substantial formation of gaps. The heat generated within the load header can be dispersed effectively to the external side by eliminating an air-layer within the load header.

8 Claims, 5 Drawing Sheets

CAPILLARY ARRAY HAVING LOAD HEADER

FIELD OF THE INVENTION

The present invention relates to a multi-capillary electrophoresis apparatus for simultaneously separating and analyzing a sample such as fluorescence-labeled nucleic acid using a plurality of capillaries.

BACKGROUND OF THE INVENTION

JP-A No. 365262/2002 (Patent Document 1) discloses a structure and a method of manufacturing a capillary array which is loaded for use into a multi-capillary electrophoresis apparatus.

The capillary array is provided with a plurality of capillaries and a window unit having an aperture for maintaining alignment of capillaries in the course of the length direction of capillaries to radiate the light to the capillaries and an aperture for detecting information depending on a sample from the capillaries. Moreover, one end of the capillary array is provided with a capillary head for binding and holding the capillaries. A sample injecting end portion of the capillary array is provided with an insulated holder, tubular electrodes fixed to the holder, and a connection plate for connecting the tubular electrodes within the holder. Moreover, there is provided a load header allocated at the upper part of the holder and formed of a cover for insulating contact portions of the connection plate and tubular electrodes from the other portion of the apparatus.

In this load header, tubular electrodes are fixed to a holder consisting of an insulated material and capillaries are inserted to the inside of corresponding tubular electrodes. The tubular electrodes are coupled with each other by the connection plate consisting of an electric conductive material and the connection plate is placed in contact with a high-voltage terminal of the electrophoresis apparatus body to simultaneously load a uniform voltage to a plurality of capillaries.

[Patent Document 1] JP-A No. 36526/2002 (Abstract)

In the load header, the tubular electrodes are fixed to the holder consisting of an insulated resin and the capillaries are inserted into such tubular electrodes. The tubular electrodes are coupled with each other by the connection plate consisting of the electric conductive material to simultaneously apply a voltage to all capillaries.

A conductive portion including the contact portions of the connection plate and tubular electrodes is insulated from the other portion with the cover provided at the upper part of holder to ensure safe operation freed from discharge or electric-shock. In this structure, an air-layer is formed among the connection plate, holder and cover within the load header.

With application of voltage during electrophoresis phenomenon, Joule heat is generated from the capillaries. The Joule heat generated from each capillary is almost equal. However, since the capillaries are arranged like a lattice in the load header and the heat can be easily transferred to the peripheral components in the capillaries located at the external side of load header, temperature of these capillaries is lowered than that of the capillaries located at the internal side (center area) of load header. Meanwhile, in the capillaries located at the internal side, since heat is not easily transferred to the peripheral materials, the heat is not easily radiated, keeping the capillaries under the high temperature condition.

Moreover, since the air-layers are formed between the connection plate and holder and between the cover and tubular electrodes within the load header, the heat insulation effect is generated, further preventing radiation of heat.

Accordingly, temperature gradient is generated depending on the locations of capillaries in the load header, bringing about fluctuation in electrophoresis velocity and resolution among the capillaries.

SUMMARY OF THE INVENTION

An object of the present invention is to effectively radiate or extract heat generated within a load header including capillaries by means of electrophoresis.

The present invention relates to technique for eliminating, as much as possible, formation of an air-layer within a load header described above. Moreover, the present invention also relates to contact between the load header and a connection plate via a higher heat conductance material. Therefore, there is provided a capillary array and an electrophoresis apparatus which can effectively radiate the Joule heat generated within the load header.

Novel features and effects of the inventions described above and the other inventions of the present invention will then be described below with reference to the accompanying drawings.

DESCRIPTION OF THE PREFERRED EMBODIMENTS

A cross-over point (COP) is considered as an index for evaluation of resolution of anelectrophoresis apparatus. COP indicates the number of bases when the half-value of the detected peak width is identical with peak width corresponding to one base in a detecting portion. Accordingly, it means that the larger this value is, the higher the resolution is. In the present invention, an average value of 96 capillaries is obtained and it is then defined as an index of the resolution.

As an index indicating fluctuation in results of electrophoresis among capillaries, a value of (maximum value−minimum value)/average value of the COP has been calculated. It means that the smaller this value is, the smaller the fluctuation among capillaries is.

Figure 7:
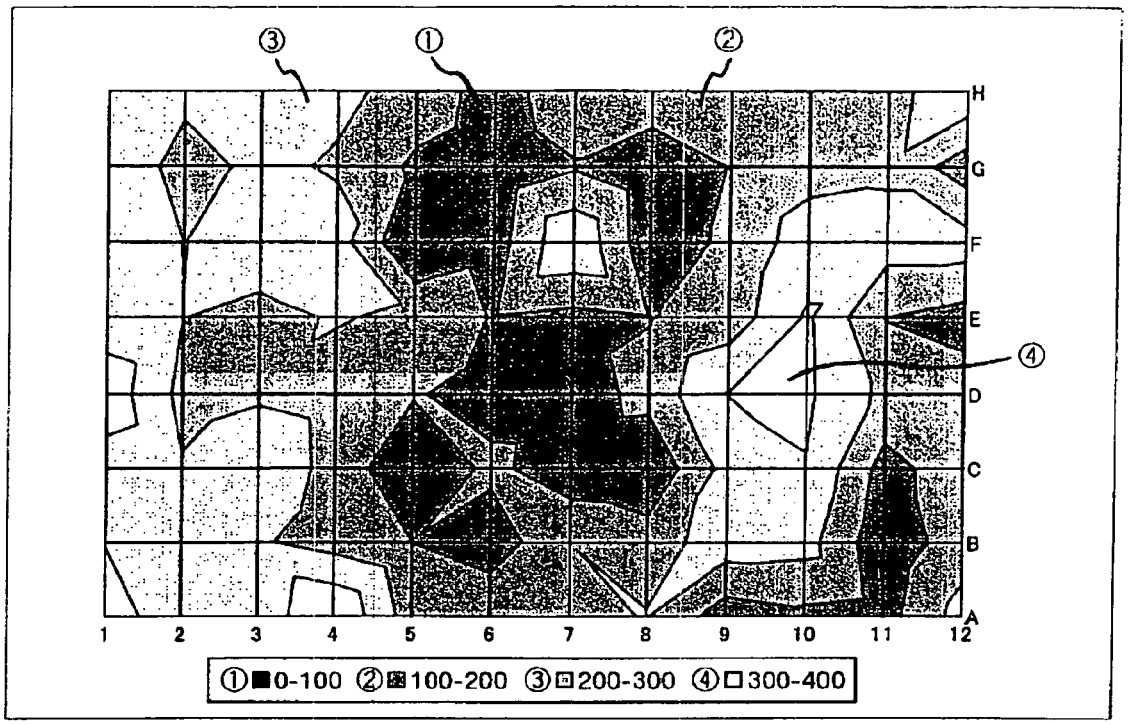
FIGS. 7A and 7B are diagrams illustrating positional relationship between the load header and capillary and results of electrophoresis in the load headers of the prior art and the present invention.
Figure 7:
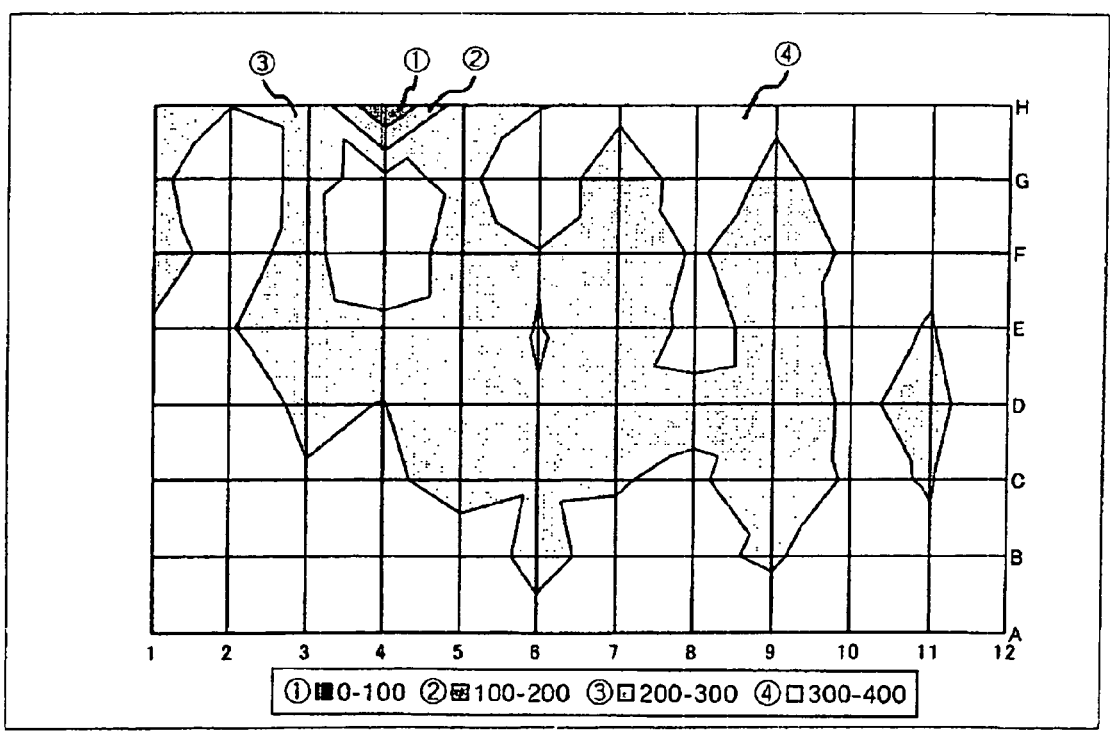

When the capillary length is 21 cm in the structure described in the patent document 1, the average value of COP has been 167 and the value of the (maximum value−minimum value)/average value of the COP has been 2.0. FIG. 7A illustrates the results of electrophoresis of each capillary allocated in the position depending on the positions on the load header. FIG. 7B illustrates the results of electrophoresis in the preferred embodiment of the present invention.

In FIGS. 7A and 7B, dark areas (①, ②), indicate that resolution indicated with the number of separated bases is low. On the contrary, the brighter the areas are (③, ④), the larger the number of bases is and the higher the resolution is. For example, in the bright area ④, the number of separated bases ranges from 300 to 400.

Here, it has been proved that the resolution of capillaries located at the center area of load header is lower than that of the capillaries located at the external area.

In the present invention, heat radiation from the capillaries and cooling function may be accelerated to reduce fluctuation in temperature among the capillaries by eliminating an air-layer which disturbs radiation of heat generated within the load header due to heat radiation of capillaries during the electrophoresis. Accordingly, fluctuation in resolution and period of the electrophoresis can be reduced. In this load header, tubular electrodes are held with an insulated holder consisting of an insulator and a sample injection end portion of each capillary is inserted into the corresponding tubular electrode.

The tubular electrodes to which the capillaries are inserted are coupled with each other within the holder through a connection plate consisting of a conductive material and when the connection plate is in contact with a high-voltage terminal of the electrophoresis apparatus body, a uniform voltage can be loaded simultaneously to a plurality of capillaries. At the upper part of the holder, a cover consisting of an insulating material is provided to cover a conductive portion including the contact portion of the connection plate and tubular electrodes. Accordingly, the conductive portion can be shielded from the other portions of the apparatus in view of preventing electric-shock to maintain safe operation.

It is desirable for elimination of the air-layer within the load header to closely place the holder, connection plate, cover and tubular electrodes in contact with each other resulting in no gap among these elements. As a raw material of the connection plate, any type of conductive material may be used but the holder, cover and tubular electrodes can be closely set by means of an elastic force by utilizing a highly flexible material such as a conductive rubber material.

It is of course possible that the connection plate and holder, cover and tubular electrodes are closely set by coating the contact surfaces of these elements with heat conductive grease or the like. In addition, it is also possible to fill the inside of load header with a filling material such as resin. The filling area may be selected to the area between the connection plate and holder and/or between the cover and tubular electrodes.

In addition, when a conductive resin is used as the filling material, the conductive resin filling the inside of load header in place of the connection plate electrically couples the tubular electrodes and substantially contacts the holder, cover and tubular electrodes each other without any gap among these elements. With these methods described above, the air-layer within the load header can be removed sufficiently and the Joule heat generated by the capillaries can be efficiently extracted to the external side. The filling material having higher heat conductance than the air may be used preferentially.

Moreover, it is desirable to use the filling material having a higher thermal capacity in order to effectively disperse the heat from the capillaries. In view of enhancing heat conductance, it is also possible to introduce combination of various materials or to use such material in addition to the use of only filling material. As an additive, for example, inorganic powder of silica, aluminum or the like and metal powder of nickel, copper or the like may be listed. As the filling material, a resin or a liquid such as grease as described above may be used. These filling materials should preferably have higher heat conductance.

First Embodiment

Figure 2:
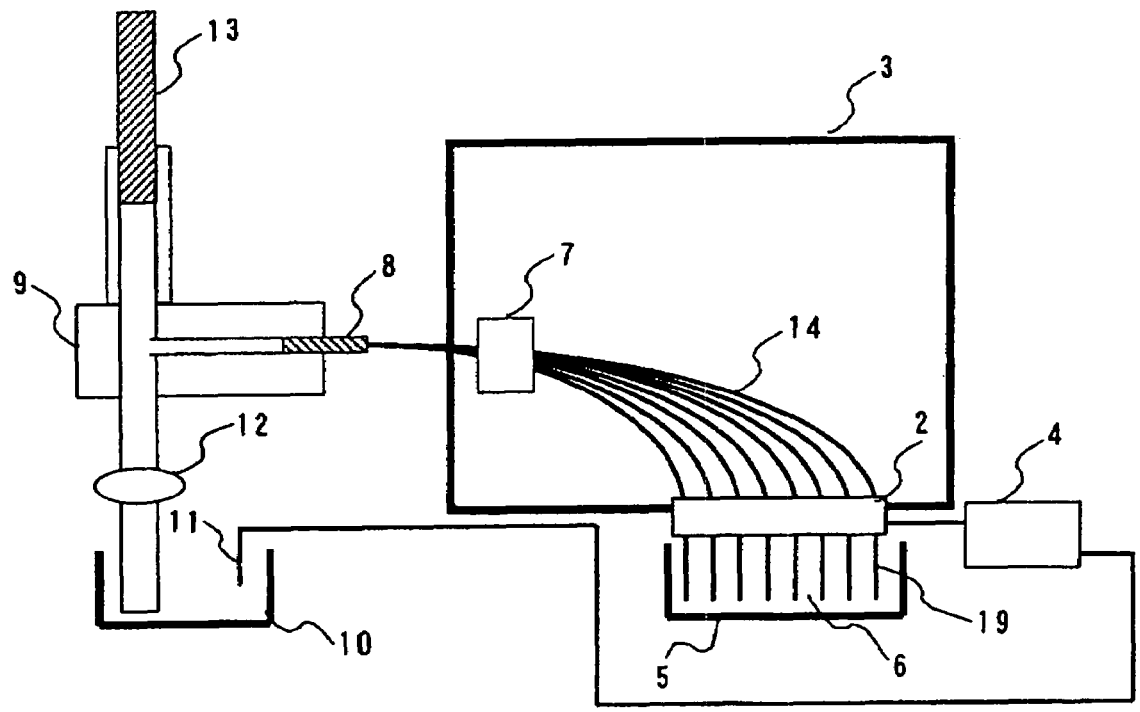
FIG. 2 is a schematic diagram of a multi-capillary electrophoresis apparatus to which the present invention is applied.

FIG. 2 schematically illustrates a multi-capillary electrophoresis apparatus to which the present invention applied. A sample injection end portion of a capillary array forms a load header 2 and is fixed to the lower part of a thermostatic bath 3. The load header 2 is connected with a power supply 4 to apply a negative voltage. For introduction of a sample into the capillaries, a negative voltage is applied under the condition that the tubular electrodes 19 to which the capillaries are inserted are soaked into the sample solution, while for the electrophoresis of sample injected into the capillaries, a negative voltage is applied under the condition that such tubular electrodes 19 are soaked into a buffer solution 6 within a first buffer container 5.

The other end portions of the capillaries are bundled to form a capillary head 8 and are connected to a pump unit 9 as a separation medium injecting mechanism. A section between the load header of the capillary array and a window unit 7 is accommodated within the thermostatic bath for the temperature management during the electrophoresis. The pump unit 9 is connected to a second buffer container 10.

The second buffer container 10 is provided with a power electrode 11 to which the capillary is inserted to form an electrophoretic passage connecting the first buffer container, capillary array, and second buffer container. When the separation medium is injected to the capillaries, the separation medium within a syringe is injected into the inside of capillary by closing a valve 12 provided to the pump unit 9 and then pushing the syringe 13. During the electrophoresis, the valve is opened to apply a voltage to the electrophoretic passage.

Figure 3:
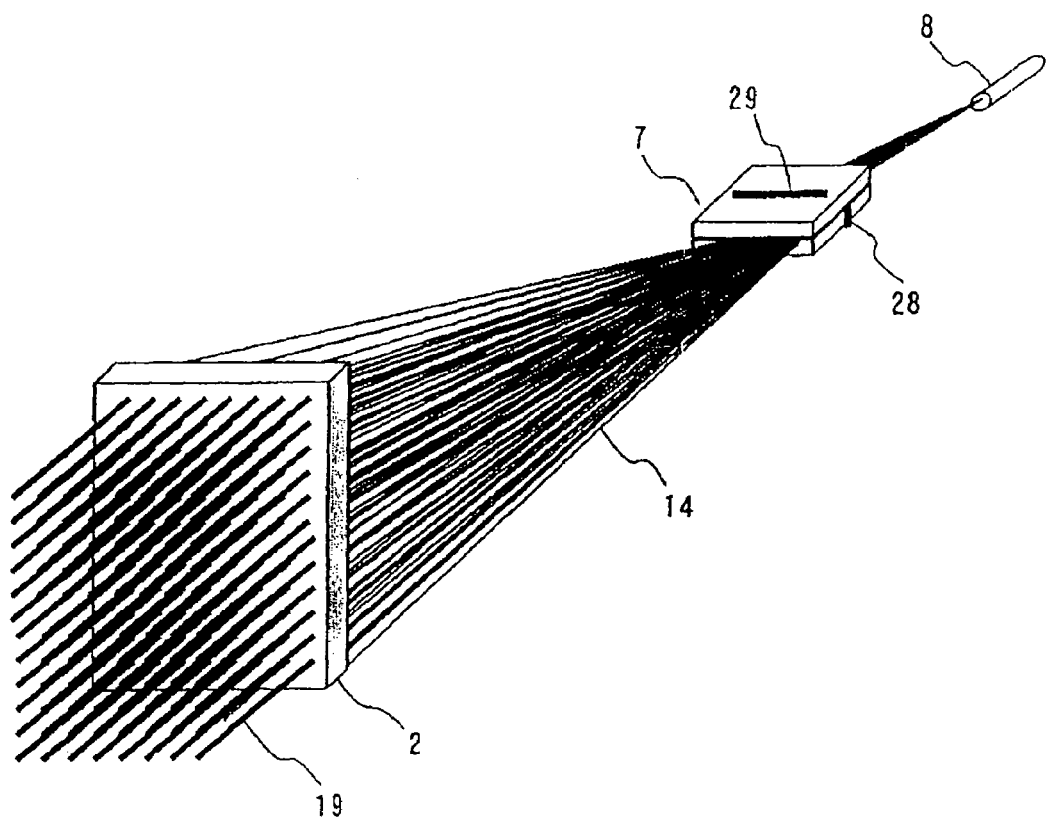
FIG. 3 is an external view of the capillary array to which the present invention is applied.

FIG. 3 illustrates an external appearance of the capillary array of FIG. 2. A capillary 14 is formed as a quartz glass tube in the external diameter of 0.1 to 0.7 mm and internal diameter of 0.02 to 0.5 mm covered at the external surface with polyimide and the capillary array is generally formed of a plurality of capillaries (ranging from several capillaries to several tens of capillaries).

The capillary array is provided with a load header 2 for taking a sample such as fluorescence-labeled nucleic acid into the capillary with the electrophoresis, a window unit 7 including apertures for maintaining the arrangement in the course of the length direction of the capillaries 14 and detecting optical radiation and signal, and a capillary head 8 for bundling and bonding the capillaries. In the present invention, the apparatus of the prior art may also be used as an optical unit which is provided with the window unit of the capillary array and a spectroscope for detecting fluorescence from the radiating portion of the window unit.

The load header 2 is provided with tubular electrodes 19 for applying a voltage to the capillaries. The cover of capillaries is removed in the window unit and moreover an aperture 28 for radiating the light to a plurality of aligned capillaries and an aperture 29 for extracting the light emitted from the capillaries are also provided. A laser beam is radiated from the direction parallel to the surface of aperture 29, namely from the aperture 28 provided at the side surface of the window unit.

Here, a DNA piece called a size marker, the number of bases of which is already known, is defined as the object of measurement. Temperature of the thermostatic bath is set to 60° C., number of capillaries is set to 96, length up to the end portion of electrode from the detecting portion (window unit) is set to 21 cm or 36 cm, a voltage per 1 cm of capillary is set to 310 V for the capillary length of 21 cm or 210 V for the capillary length of 36 cm.

Figure 1:
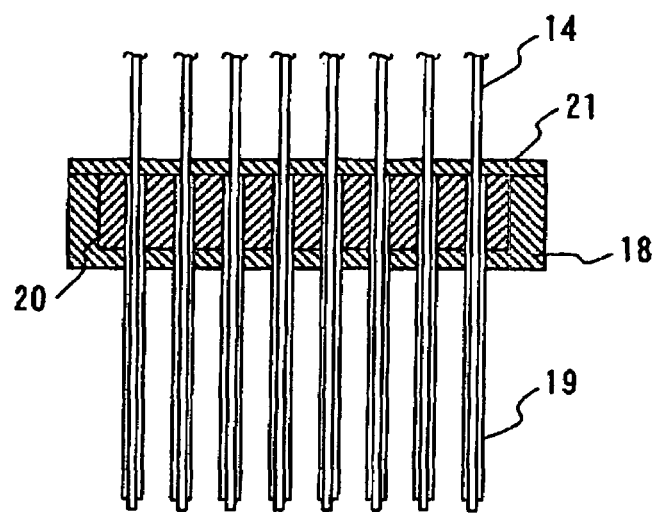
FIG. 1 is a cross-sectional view of a load header of a capillary array as a first embodiment of the present invention.

A cross-sectional view of the load header of this embodiment is illustrated in FIG. 1. Here, there is provided a capillary array where a connection plate 20 is set closely to a holder 18, a cover 21, and tubular electrodes and an air-layer does not exist within the load header. When such structure is formed and the capillary length is set to 21 cm, the average value of COP has been 304 and a value of (maximum value−minimum value)/average value of capillary has been 0.4.

Figure 8:
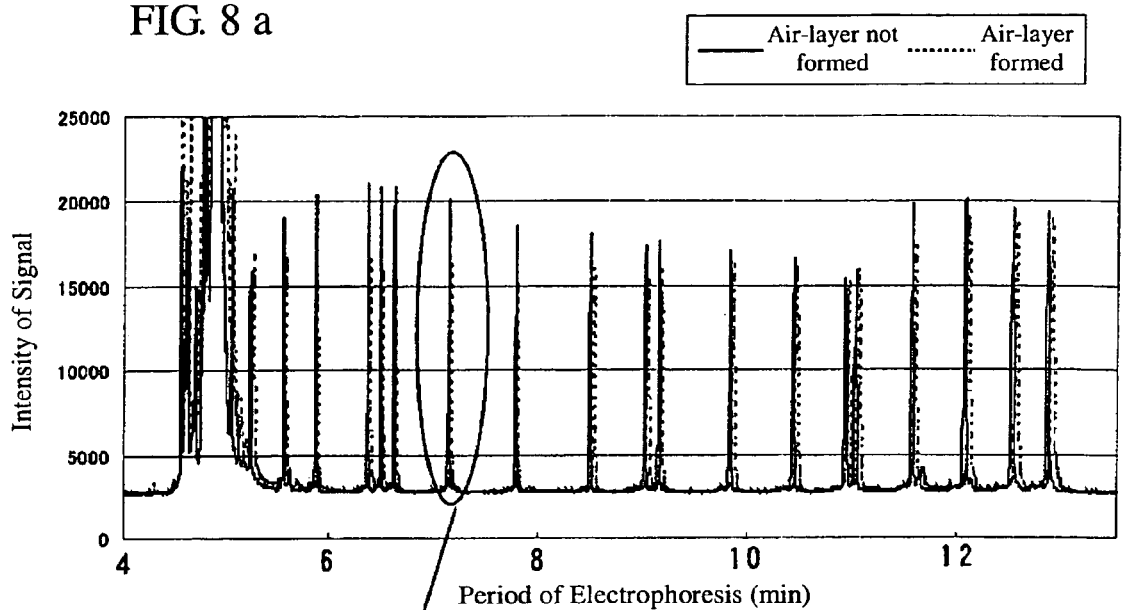
FIGS. 8A and 8B are diagrams illustrating the signals obtained with the capillary located at 6 D of the capillary array of the first embodiment of the present invention.
Figure 8:
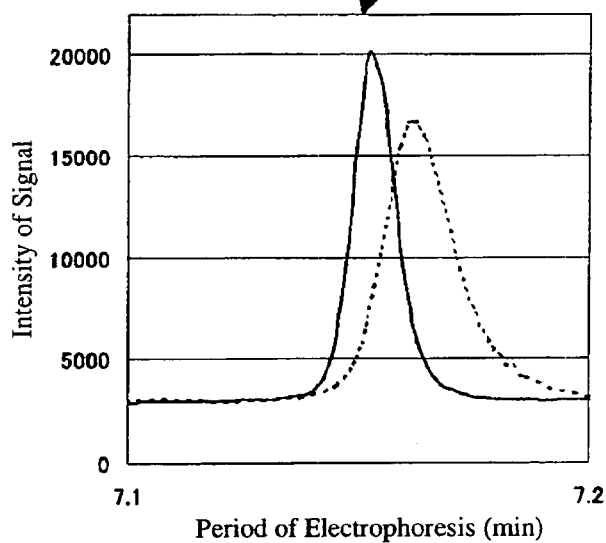

FIG. 7B illustrates results of electrophoresis of each capillary arranged depending on the positions on the load header. In comparison with FIG. 7A, the resolution of capillaries located at the center area of the load header is improved and total fluctuation is also lowered. FIG. 8A illustrates signals obtained from the capillaries located at almost the center area of the load header (corresponding to 6 D in FIGS. 7A and 7B).

FIG. 8B illustrates detail of an enlarged peak surrounded by a circle. The signal obtained from the capillary array including the air-layer within the load header is illustrated with a dotted line in FIG. 8A, while the signal obtained using the capillary array including no air-layer within the load header illustrated in FIG. 1 based on this embodiment is illustrated with a solid line in FIG. 8A.

The signal obtained from the capillary array of this embodiment is improved in the resolution because each peak width of this signal is rather narrow in comparison with that of the signal obtained from the capillary array including the air-layer within the load header. According to this embodiment, the resolution of 100 bases or more and reduction effect in fluctuation can be obtained when the capillary length is 21 cm.

When the capillary length is 36 cm, the average value of the COP has been 599 and the value of (maximum value−minimum value)/average value of the COP has been 0.16. Meanwhile, when the capillary array including no air-layer within the load header as illustrated in FIG. 1 is used, the average value of the COP has been 634 and the value of the (maximum value−minimum value)/average value of the COP has been 0.04. As illustrated in FIG. 8B, it can be understood that when the air-layer is formed, a half-value width is larger than that while the air-layer is not formed and thereby the resolution is reduced as much as the half-maximum.

According to this embodiment, improvement in the resolution of 35 bases and reduction effect in fluctuation have been proved when the capillary length is 36 cm. When the capillary length is shorter, larger effect has been expected in the present invention.

Second Embodiment

Figure 4:
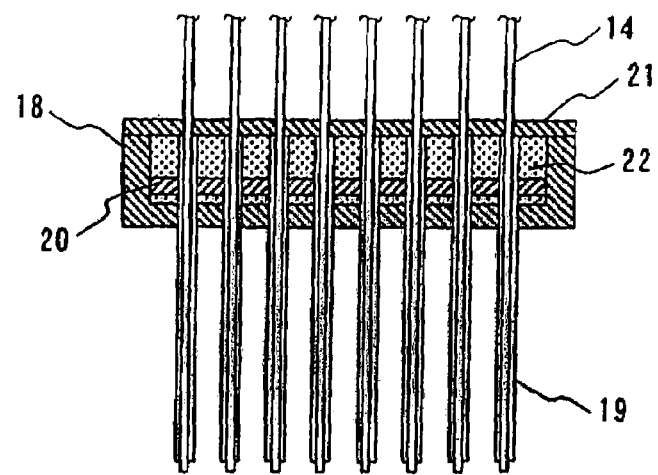
FIG. 4 is a cross-sectional view of the load header of the capillary array as a second embodiment of the present invention.

FIG. 4 is a cross-sectional view of the load header of capillary array according to the second embodiment. Difference from the first embodiment is that the air-layer formed within the load header has substantially been eliminated by filling the gaps among the connection plate, holder 18 and cover 21 with heat conductive grease 22. When such capillary array is used and the capillary length is 21 cm, the average value of the COP has been 300, while the value of the (maximum value−minimum value)/average value of the COP has been 0.53.

When the capillary length is 36 cm, such values have been 635 and 0.05 respectively. According to this second embodiment, improvement in resolution of 100 bases or more and reduction effect in fluctuation have been attained when the capillary length is 21 cm in comparison with the case that the air-layer is formed within the load header, while improvement in resolution of about 35 bases and reduction effect in fluctuation have been attained when the capillary length is 36 cm.

Third Embodiment

Figure 5:
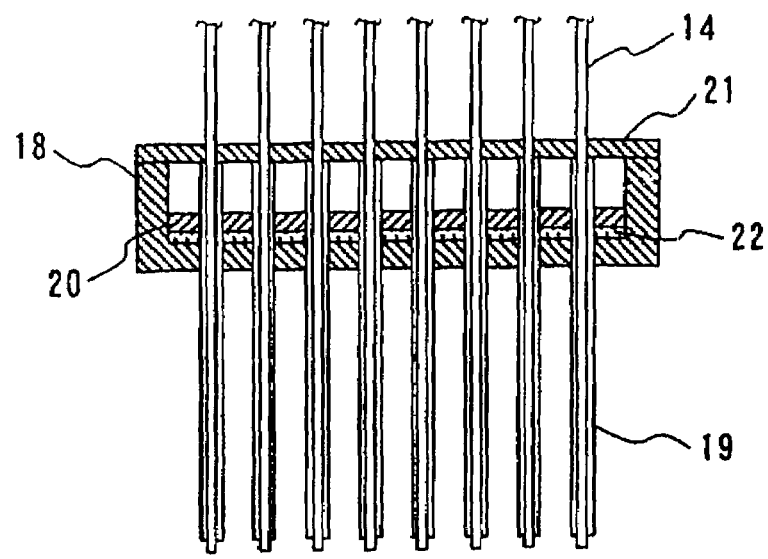
FIG. 5 is a cross-sectional view of the load header of the capillary array as a third embodiment of the present invention.

FIG. 5 is a cross-sectional view of the load header of capillary array of the third embodiment. Difference from the second embodiment is that the heat conductive grease 22 has been applied only to the gap between the holder 18 and connection plate 20. When such capillary array is used and the capillary length is 21 cm, the COP value has been 274, while the value of the (maximum value−minimum value)/average has been 0.45. When the capillary length is 36 cm, these values have been 632, and 0.06 respectively.

According to this embodiment, when the capillary length is 21 cm, improvement in resolution of about 100 bases and reduction effect in fluctuation have been attained in comparison with that of the case that the air-layer is formed within the load header, while when the capillary length is 36 cm, improvement in resolution of about 30 bases and reduction effect in fluctuation have been attained.

Fourth Embodiment

Figure 6:
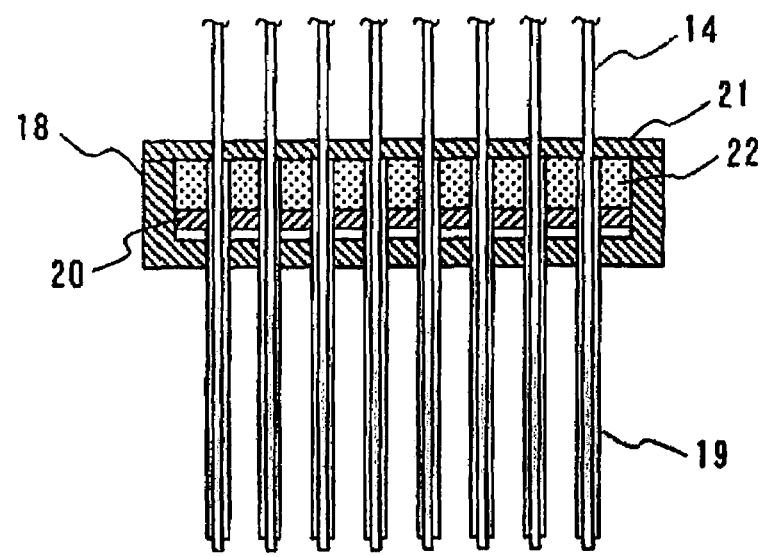
FIG. 6 is a cross-sectional view of the load header of the capillary array as a fourth embodiment of the present invention.

FIG. 6 is a cross-sectional view of the load header of capillary array according to the other embodiment. Difference from the second embodiment is that the heat conductive grease 22 has been applied only to the gap between the connection plate 20 and cover 21. When such capillary array is used and the capillary length is 21 cm, the average value of the COP has been 270, while the value of (maximum value−minimum value)/average value of the COP has been 0.55.

As described above, according to this fourth embodiment, reduction in fluctuation and improvement in resolution of the electrophoresis depending on the capillary position on the load header can be obtained. When the capillary length is 36 cm, the average value of the COP has been 634 and the value of the (maximum value−minimum value)/average value of the COP has been 0.05. According to this embodiment, when the capillary length is 21 cm, improvement in resolution of about 100 bases and reduction effect in fluctuation have been attained, in comparison with the case that the air-layer is formed within the load header 2. When the capillary length is 36 cm, improvement in resolution of about 30 bases and reduction effect in fluctuation have been attained.

According to the present invention, heat generated within the load header can be dispersed effectively to the external side in the multi-capillary array used for the multi-capillary electrophoresis apparatus.

What is claimed is:

1. A capillary array comprising:
   a plurality of capillaries for holding a separation medium for separating a sample;
   a detecting portion for maintaining alignment of the capillaries;
   a capillary head for bundling and holding capillaries to one end of the capillaries; and a load header including an insulated holder, a conductive connection plate and an insulating member and for supporting tubular electrodes, wherein the insulated holder is provided at sample injection end portions of the capillaries;

the tubular electrodes are fixed to the insulated holder, to allow insertion of sample injection end portions of capillaries;

the conductive connection plate has bores for insertion of the tubular electrodes, supported by the insulated holder and electrically connects the tubular electrodes with each other;

the insulating member and the insulated holder surround a conductive portion including a connecting portion between the conductive connection plate and the tubular electrodes in collaboration with the insulating holder and electrically insulates the connecting portion from the other portions; and the insulated holder, the insulating member, the conductive connection plate and the tubular electrodes are substantially closely arranged so as to make no gaps around the tubular electrodes in the load header.

2. The capillary array according to claim 1, wherein a filling material is applied to a gap between the insulated holder and conductive connection plate and/or to a gap between the conductive connection plate and insulating member.

3. The capillary array according to claim 2, wherein the filling material includes inorganic powders or metal powders and has higher heat conductance than the air.

4. The capillary array according to claim 3, wherein a conductive resin is substituted for the conductive connection plate within the load header to electrically connect the tubular electrodes with each other.

5. An electrophoresis apparatus comprising:

a capillary array comprising:

a plurality of capillaries for holding a separation medium for separating a fluorescence labeled sample;

a detecting portion for maintaining alignment of the capillaries;

a capillary head for bundling and holding capillaries to one end of the capillaries;

a load header including an insulated holder, a conductive connection plate and an insulating member and for supporting tubular electrodes, wherein the insulated holder is provided at sample injection end portions of the capillaries;

the tubular electrodes are fixed to the insulated holder, to allow insertion of sample injection end portions of capillaries;

the conductive connection plate has bores for insertion of the tubular electrodes, supported by the insulated holder and electrically connects the tubular electrodes with each other;

the insulating member and the insulated holder surround a conductive portion including a connecting portion between the conductive connection plate and the tubular electrodes in collaboration with the insulating holder and electrically insulates the connecting portion from the other portions; and the insulated holder, the insulating member, the conductive connection plate and the tubular electrodes are substantially closely arranged so as to make no gaps around the tubular electrodes in the load header.

6. The electrophoresis apparatus according to claim 5, wherein a filling material is applied to a gap between the insulated holder and conductive connection plate and/or to a gap between the conductive connection plate and insulating member.

7. The electrophoresis apparatus according to claim 6, wherein the filling material includes inorganic powders or metal powders and has higher heat conductance than the air.

8. The electrophoresis apparatus according to claim 7, wherein a conductive resin is substituted for the conductive connection plate within the load header to electrically connect the tubular electrodes with each other.

* * * * *